(12) United States Patent
Funk et al.

(10) Patent No.: US 9,214,311 B2
(45) Date of Patent: Dec. 15, 2015

(54) METHOD AND APPARATUS FOR TRANSMISSION OF FLUORESCENCE X-RAY RADIATION USING A MULTILAYER X-RAY TARGET

(71) Applicant: TRIPLE RING TECHNOLOGIES, INC., Newark, CA (US)

(72) Inventors: Tobias Funk, Martinez, CA (US); Brian Patrick Wilfley, Los Altos, CA (US)

(73) Assignee: Triple Ring Technologies, Inc., Newark, CA (US)

( * ) Notice: Subject to any disclaimer, the term of this patent is extended or adjusted under 35 U.S.C. 154(b) by 226 days.

(21) Appl. No.: 13/928,255

(22) Filed: Jun. 26, 2013

(65) Prior Publication Data
US 2013/0287177 A1 Oct. 31, 2013

Related U.S. Application Data

(63) Continuation-in-part of application No. 13/304,030, filed on Nov. 23, 2011, now Pat. No. 8,848,867.

(60) Provisional application No. 61/417,396, filed on Nov. 26, 2010.

(51) Int. Cl.
*G01N 23/04* (2006.01)
*H01J 35/08* (2006.01)
*A61B 6/00* (2006.01)
*H01J 35/14* (2006.01)

(52) U.S. Cl.
CPC .............. *H01J 35/08* (2013.01); *A61B 6/4035* (2013.01); *A61B 6/4064* (2013.01); *H01J 35/14* (2013.01); *H01J 2235/087* (2013.01)

(58) Field of Classification Search
CPC .................... H01J 2235/081; H01J 2235/088; H01J 35/08; H01J 35/14; A61B 6/4064; A61B 6/4035
USPC .................................. 378/119, 143, 121, 145
See application file for complete search history.

(56) References Cited

U.S. PATENT DOCUMENTS 4,622,688 A * 11/1986 Diemer et al. ................ 378/143

OTHER PUBLICATIONS

Gaines, J. L., et al. "Facilities and techniques for x-ray diagnostic calibration in the 100-eV to 100keV energy range." Proceedings of SPIE, 30th Annual Technical Symposium on Optical and Optoelectronic Applied Sciences and Engineering, Aug. 1986. USA.

* cited by examiner

*Primary Examiner* — Courtney Thomas
(74) *Attorney, Agent, or Firm* — Sabrina N. David; Joseph T. Lin (57) ABSTRACT

The present invention pertains to a method and apparatus for generating a beam of charged particles, accelerating the charged particles toward a first side of a layer of X-ray target material configured to emit Bremsstrahlung radiation through a second side, receiving the Bremsstrahlung radiation on a first face of an additional layer of a different X-ray target material configured to emit characteristic fluorescence X-rays with energy above 20 keV through a second face, wherein the additional layer of X-ray target material is located within 3 mm of the second side of the first layer of material. The first X-ray target material can have an atomic number greater than 21.

17 Claims, 6 Drawing Sheets

METHOD AND APPARATUS FOR TRANSMISSION OF FLUORESCENCE X-RAY RADIATION USING A MULTILAYER X-RAY TARGET

RELATED U.S. APPLICATION

This application is a continuation-in-part of the co-pending U.S. non-provisional patent application Ser. No. 13/304,030, entitled "Method and Apparatus for Adaptive Exposure in X-ray Systems," filed Nov. 23, 2011, which is hereby incorporated by reference in its entirety.

FIELD OF THE INVENTION

The present invention is in the field of X-ray sources. The present invention is also in the field of X-ray generating targets for X-ray sources.

BACKGROUND

Many medical imaging procedures utilize X-ray radiation because X-rays are of energies, or wavelengths, that can penetrate most human tissue but are also absorbed or scattered to differing degrees by relatively dense tissue of organs and by bone. This property is useful as the relative intensity of X-rays emerging from a given irradiated region of a patient will correspond to the "X-ray density," i.e., the propensity to attenuate X-rays, of the internal structures within that region. Collected by an X-ray detector or simply incident on a fluorescent screen or X-ray film, emerging X-rays can be used to image the internal structures of the region. Furthermore, implements such as catheters may be inserted into a patient for surgical purposes and be tracked using X-ray imaging, or X-ray dense fluids may be injected into patients' veins so that blood vessel networks can be highlighted in subsequent X-ray images.

Some X-ray imaging procedures irradiate the patient for only a short period of time, as less than a second may be required to collect enough intensity data for a single X-ray image. However, some X-ray imaging is completed on a continuous basis such that a real-time video is generated for fluoroscopy and other image-guided procedures. Many surgeries, including the placement of stents and other cardiac procedures, have become much safer and requiring of significantly less recovery time since real-time X-ray imaging systems have enabled less invasive procedures.

While X-ray imaging is widely used for the aforementioned reasons, health risks associated with excessive exposure to high energy radiation, including X-rays, are recognized. The interaction of radiation with human cells and tissues may induce breakages or mutations which can develop into cancers over time. The probability of this type of cellular damage may be relatively insignificant from the exposure necessary to take a single image, as may be necessary to analyze a broken bone, but may become less insignificant for patients who undergo relatively lengthy image-guided procedures, require multiple CAT scans, or undergo other multi-frame X-ray imaging procedures. Furthermore, cumulative amounts of scattered X-ray radiation may pose health risks for medical personnel attending X-ray imaging procedures on a regular basis.

Precautions taken in medical settings against significantly increasing individuals' cancer risk through X-ray exposure have included attaching collimation devices to X-ray sources which attenuate X-rays travelling in directions away from the region to be imaged and providing physical shielding for attendant personnel. Use of non-conventional X-ray imaging configurations such as inverse geometry systems have been explored to lower the overall amount of X-ray exposure necessary to obtain good-quality X-ray images by reducing scatter noise or other factors that degrade image quality.

However, existing precautions do little to tailor the amount of X-ray radiation being used during an imaging procedure to the specific patient, or regions within the patient, to reduce the amount of radiation exposure. What is needed is an imaging system capable of producing rapid high quality images while reducing the amount of radiation exposure.

Use of beam hardening filters, which may filter out a number of the lowest energy components of an X-ray energy spectrum, is another method that has been explored for reducing exposure and improving image quality. However, such filters can only remove the relatively lowest energy X-rays and can be difficult to implement effectively. What is needed is an X-ray source providing a relatively monoenergetic spectrum of generated X-rays. What is further needed is an X-ray source capable of providing such an X-ray beam with a well-defined focal spot. Such an X-ray source could enable further applications of X-ray technology in the medical, security, metrology, and other fields.

SUMMARY

The present invention pertains to a method and apparatus for generating a beam of charged particles, accelerating the charged particles toward a first side of a first layer of an X-ray target material that is configured to emit Bremsstrahlung radiation through a second side, receiving the Bremsstrahlung radiation on a first face of a second layer of a different X-ray target material that is configured to emit characteristic fluorescence X-rays with energy above 20 keV through a second face of the layer, wherein the second layer is located within 3 mm of the second side of the first layer.

The material of the first layer can have an atomic number greater than 21, and may be tungsten or molybdenum. The material of the second layer can have a characteristic X-ray fluorescence energy above 20 keV or further above 80 keV, and may be uranium or bismuth. The thickness of the first layer may in one embodiment be between 1 μm and 50 μm and in another between 200 μm and 800 μm. The thickness of the second layer may be between 100 μm and 500 μm.

An X-ray collimator can be provided and configured for selective transmission of X-rays emitted at a predetermined non-zero angle from the axis of travel of the charged particle beam, wherein said predetermined non-zero angle may be greater than 50 degrees and in one embodiment may be between 75 and 85 degrees. The two target layers may be in contact with one another. Alternatively, a thermally conductive material or a cooling fluid system may be provided between the layers.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

X-ray generation can occur from two different physical phenomena: Bremsstrahlung and X-ray fluorescence. Bremsstrahlung can refer to the emission of electromagnetic radiation that can occur when fast-moving charged particles are stopped or slowed down. The energy of the resulting electromagnetic radiation can be dependent on the initial energy of the particles and types of particle interactions involved in the stopping or slowing and may therefore vary across a relatively wide spectrum of X-ray energies. X-ray fluorescence can occur when an electron in an inner shell of an atom absorbs a photon having energy greater than the binding energy of the atomic subshell and thereby escapes from the atom, leaving a vacancy in the inner shell. An outer shell electron can then release energy in the form of an X-ray fluorescence photon in order to transition to the relatively lower energy state of the inner shell and fill the vacancy. As these processes are inherently related to the atomic structure of the material, X-ray fluorescent photons emitted from a material can only have one of a few discrete energy values associated with or characteristic of that material.

Figure 1:
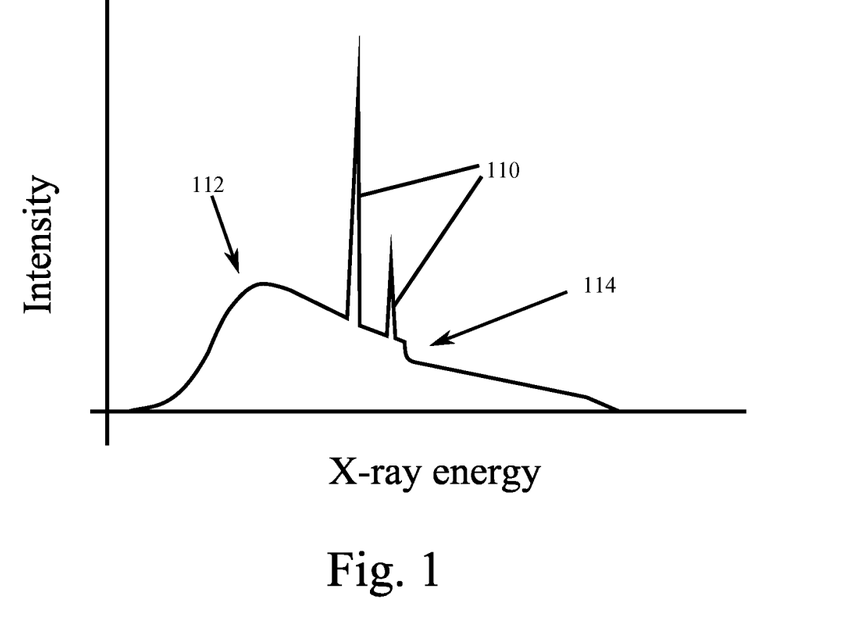
FIG. 1 is a diagram showing an exemplary X-ray spectrum from an X-ray source.

FIG. 1 is a diagram showing an exemplary X-ray spectrum from an X-ray source. Bremsstrahlung X-rays 112 are shown spanning a relatively wide energy spectrum, e.g., as previously described. A drop in the amount of Bremsstrahlung radiation can be noted at the K-edge 114, an energy level also associated with the atomic structure of a target material. In addition to the relatively continuous features of Bremsstrahlung radiation 112, one or more fluorescence peaks 110 can occur in the spectrum. Fluorescence peaks 110 can occur at discrete energy levels associated with an X-ray target material. In one embodiment of the present invention, an X-ray source can be configured to produce a relatively more monoenergetic X-ray spectrum, such as a spectrum primarily comprising only one or a few fluorescence peaks 110.

Figure 2:
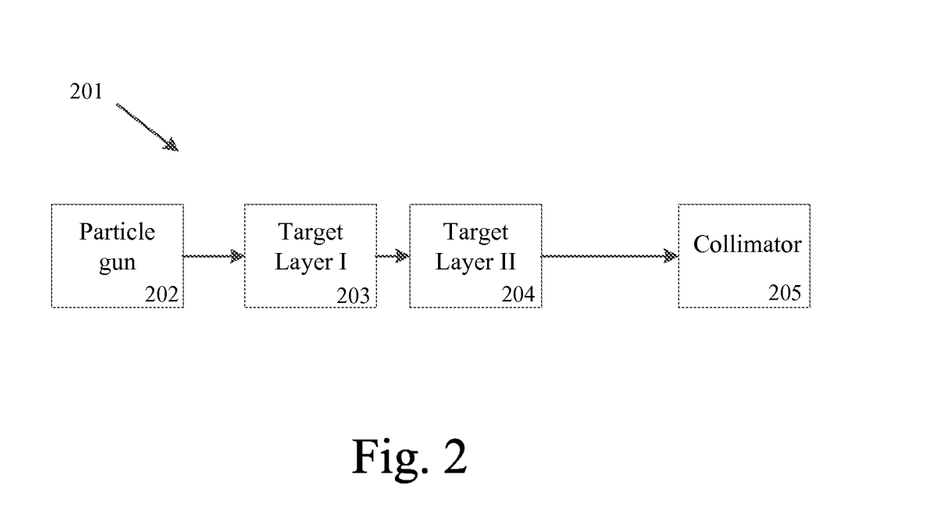
FIG. 2 is a block diagram showing an X-ray source of one embodiment of the present invention.

FIG. 2 is a block diagram showing an X-ray source of one embodiment of the present invention. In this embodiment, an X-ray source 201 can comprise a multilayer target. A first target layer 203, e.g., located nearer to a particle gun 202 than a second target layer 204, can be configured to produce Bremsstrahlung radiation when struck by particles from particle gun 202. First target layer 203, may, for example, comprise a layer having an atomic weight and thickness sufficient for stopping a predetermined amount of incident charged particles and for emitting Bremsstrahlung X-rays in a forward or transmission direction, e.g., from a face opposite the face receiving charged particles. First target layer 203 may, for example, be a material having an atomic number greater than 21, 39, or 71, inclusive, or any other atomic number between or above the enumerated values. First target layer 203 may also be a material having an atomic number greater than 49, 59, or 69, or any other atomic number between or above the enumerated values. First target layer 203 may also have a melting point above 1000K. First target layer 203 may further have a melting point above 1200K, 1350K, or 1500K, or another temperature between or above the enumerated values.

In this embodiment second target layer 204 may be configured to emit fluorescence X-rays, including but not limited to K-line or L-line emission, upon receiving Bremsstrahlung radiation from first target layer 203. Second target layer 204 may be configured to emit X-rays, e.g., fluorescence X-rays, through a surface or face other than that surface or face receiving radiation from first target layer 203, e.g., in a transmission direction. In one embodiment, second target layer 204 may be a material having at least one characteristic X-ray fluorescence energy above 20 keV. Second target layer 204 may alternatively be a material having at least one characteristic X-ray fluorescence energy above 30 keV, 40 keV, 50 keV, 60 keV, 70 keV, or 80 keV, inclusive, or any other energies between or above the enumerated values.

In one embodiment of the present invention, second target layer 204 may be in contact with first target layer 203. In another embodiment of the present invention, second target layer 204 may be positioned within 3 mm from first target layer 203. Second target layer 204 may further be positioned within 2 mm, 1 mm, 800 µm, 600 µm, 400 µm, 200 µm, 80 µm, 60 µm, 40 µm, 20 µm, or 10 µm from first target layer 203. A thermally conductive material may be provided between the layers. In another embodiment of the present invention a cooling system may be configured to flow cooling fluid, e.g., water or other coolant, between first target layer 203 and second target layer 204. A cooling system may also or alternatively be configured to flow cooling fluid on outside faces of the layers, e.g., on an outer face of second target layer 204.

A collimator 206 may optionally be provided for collimation of fluorescence X-rays or X-ray beam from second layer 204. Collimator 206 may be positioned along a common axis with first target layer 203 and second target layer 204, e.g., an axis of travel of the charged particle beam, but may also be positioned at an angle relative to the axis of particle beam travel, and may be specifically positioned to transmit fluorescence X-rays. Particle gun 202 may comprise a source of electrons or other charged particles and components configured for accelerating or focusing the charged particles onto first target layer 203.

In one embodiment of the present invention, particle gun 202, first target layer 203, and second target layer 204 can be housed within a vacuum chamber of source 201. Vacuum can be maintained around the path of a charged particle beam from particle gun 202. In another embodiment, first target layer 203 can be provided within or as part of the vacuum chamber, e.g., such that second target layer 204 may be outside of vacuum. In another embodiment, second target layer 204, or a support structure around second target layer 204 may be provided as part of the vacuum chamber.

Figure 3:
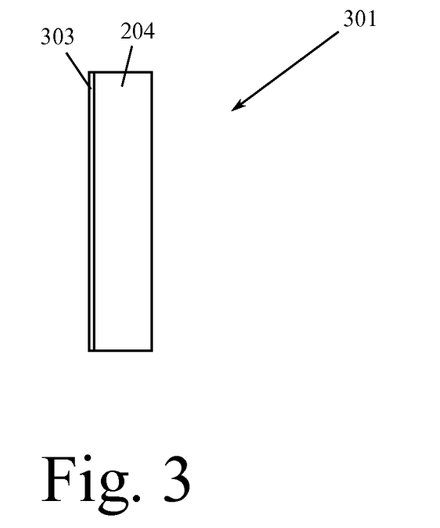
FIG. 3 is a diagram showing an exemplary multilayer X-ray target for an X-ray source of an embodiment of the present invention.

FIG. 3 is a diagram showing an exemplary multilayer X-ray target for an X-ray source of an embodiment of the present invention. In the embodiment of FIG. 3, a first target layer 303 of multilayer target 301 can be relatively thin. First target layer 303 can, for example, be less than 100 μm. First target layer 303 may also be less than 70 μm, 50 μm, or 30 μm. In one embodiment, first target layer 303 may be between 1 μm and 50 μm, 10 μm and 40 μm, 20 μm and 30 μm, 22 μm and 28 μm, or 24 μm and 26 μm, inclusive, or any other integer or non-integer number of microns within or between the enumerated ranges. First target layer 303 can comprise a material having properties suited to producing Bremsstrahlung radiation without melting at the above enumerated thicknesses. In one such embodiment, first target layer 303 can comprise tungsten.

In the embodiment of FIG. 3, second target layer 204 can have a thickness between 100 μm and 500 μm, inclusive, or any other integer or non-integer number of microns within the enumerated range. For example, second target layer 204 may have a thickness of exactly or approximately 200 μm, 250 μm, 300 μm, 350 μm, or 400 μm. In one embodiment, layer 204 can have a thickness between 275 μm and 325 μm, inclusive. Second target layer 204 may comprise a material having a K-shell binding energy or K-edge less than the Bremsstrahlung X-ray energies to be emitted from first target layer 303. Bremsstrahlung X-ray energies may be predicted from the voltage of particle gun 202, e.g., in conjunction with properties of first target layer 303. A particle gun 202 voltage may be any voltage between 20 kVp and 300 kVp, inclusive. Particle gun 202 voltage may further be between 80 kVp and 280 kVp, 100 kVp and 260 kVp, 110 kVp and 250 kVp, or 120 kVp and 230 kVp, inclusive, or have any other peak voltage within or between the enumerated ranges. In these embodiments, Bremsstrahlung X-rays may be produced from first target layer 303 having energies up to 300 keV, 280 keV, 260 keV, 250 keV, or 230 keV, inclusive, or any other energies between or below the enumerated values. In one embodiment of the present invention, second target layer 204 can comprise uranium. In another embodiment, second target layer 204 can comprise bismuth.

In one embodiment of the present invention, multilayer target 301 of the embodiment of FIG. 3 can be fabricated by sputtering material of first target layer 303 onto a foil, microfoil, or sheet of second target layer 204 material. Any other manner of depositing a thin layer or film of first target layer material onto second target layer 204 may be utilized, including but not limited to chemical vapor deposition, electrospraying, or other techniques. In another embodiment of the present invention, a foil, microfoil, or sheet of the material of first target layer 303 can be positioned in contact with or bonded to a foil, microfoil, or sheet of material of second target layer 204. In another embodiment, a foil, microfoil, or sheet of the material of first target layer 303 can be positioned within 3 mm of a foil, microfoil, or sheet of material of second target layer 204, and space between said first target layer 303 and said second target layer 204 can be filled with a thermally conductive material or thermal interface material. In one such embodiment, the thermally conductive material may be a thermal grease, including but not limited to a ceramic-based, metal-based, carbon-based, or liquid metal-based thermal grease.

In another embodiment, first target layer 303 and second target layer 204 can be brazed to one another. A braze material in this embodiment can include without limitation aluminum, silicon, copper, silver, zinc, gold, nickel, iron, boron, phosphorous, indium, and gallium, and any alloys or combinations thereof. The braze material may be configured to remain solid during X-ray generation, e.g., have a melting point above temperatures achieved by first target layer 204 during X-ray generation, or may be configured to melt or be in liquid form during X-ray generation.

Figure 4:
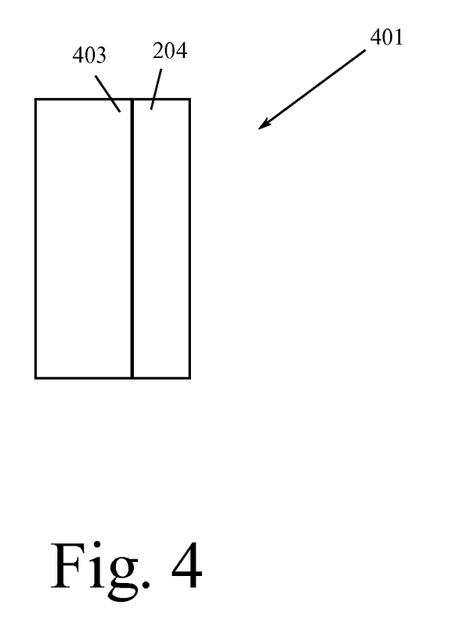
FIG. 4 is a diagram showing another exemplary multilayer X-ray target for an X-ray source of an embodiment of the present invention.

FIG. 4 is a diagram showing another exemplary multilayer X-ray target for an X-ray source of an embodiment of the present invention. In the embodiment of FIG. 4, a first target layer 403 of multilayer target 401 can be thicker than in the embodiment of FIG. 3. First target layer 403 can, for example, be at least 100 μm. First target layer 403 may also be more than 200 μm, 300 μm, or 400 μm. In one embodiment, first target layer 403 may be between 200 μm and 800 μm, 400 μm and 600 μm, 450 μm and 550 μm, or 475 μm and 525 μm, inclusive, or any other integer or non-integer number of microns within or between the enumerated ranges. First target layer 403 can comprise a material having properties suited to producing Bremsstrahlung radiation without melting at the above enumerated thicknesses. In one such embodiment, first target layer 303 can comprise molybdenum. In another embodiment, first target layer 303 can comprise copper.

In the embodiment of FIG. 4, second target layer 204 can have a thickness between 100 μm and 500 μm, inclusive, or any other integer or non-integer number of microns within the enumerated range. For example, second target layer 204 may have a thickness of exactly or approximately 200 μm, 250 μm, 300 μm, 350 μm, or 400 μm. In one embodiment, layer 204 can have a thickness between 275 μm and 325 μm, inclusive. Second target layer 204 may comprise a material having a K-edge less than the predicted Bremsstrahlung X-ray energies from first target layer 403. Bremsstrahlung X-ray energies may be predicted from particle gun 202 voltage, e.g., any of the particle gun voltages previously enumerated, possibly in conjunction with properties of first target layer 403. In one embodiment of the present invention, second target layer 204 can comprise uranium. In another embodiment, second target layer 204 can comprise bismuth.

In one embodiment of the present invention, multilayer target 401 of the embodiment of FIG. 4 can be fabricated by bonding, e.g., thermally or by any other method, a sheet or foil of the material of first target layer 403 with a sheet or foil of the material of second target layer 204. Any other manner of manufacturing multilayer target 401 may be utilized, including but not limited to brazing two sheets or foils together, electrospraying one layer onto the other, or positioning the two layers a predetermined distance from one another. A thermally conductive material or thermal interface material may be provided between the layers. In one such embodiment, the thermally conductive material may be a thermal grease, including but not limited to a ceramic-based, metal-based, carbon-based, or liquid metal-based thermal grease.

In another embodiment, first target layer 403 and second target layer 404 can be brazed to one another. A braze material in this embodiment can include without limitation aluminum, silicon, copper, silver, zinc, gold, nickel, iron, boron, phosphorous, indium, and gallium, and any alloys or combinations thereof. The braze material may be configured to remain solid during X-ray generation, e.g., have a melting point above temperatures achieved by first target layer 204 during X-ray generation, or may be configured to melt or be in liquid form during X-ray generation.

In the embodiments of FIG. 3 and FIG. 4 and similar embodiments of the present invention, a multilayer target faces may be circular, polygonal, square, ellipsoidal, rectangular, or any other shape. The target may have a height, e.g., or diameter, between 0.5 mm and 10 mm, inclusive, excluding additional material that may be provided for bonding of housing structures or other elements of the source around edges of the target. The target may further have a height, e.g., or diameter, between 1 mm and 6 mm, 1.5 mm and 5.5 mm, or 2 mm and 5 mm, inclusive, or any other integer or non-integer number of millimeters within or between the enumerated ranges.

Figure 5:
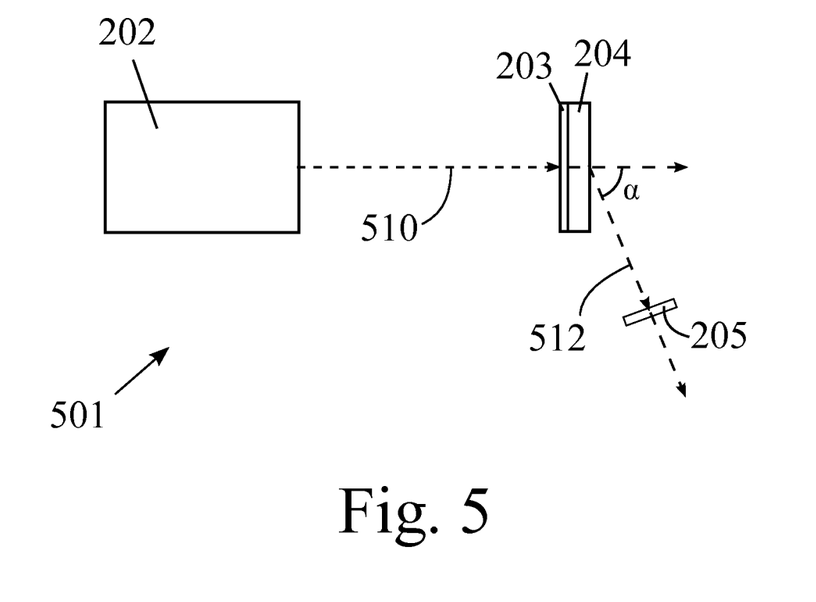
FIG. 5 is a diagram showing an X-ray source configuration having an X-ray collimator positioned at a predetermined angle from a charged particle beam axis of one embodiment of the present invention.

FIG. 5 is a diagram showing an X-ray source configuration having an X-ray collimator positioned at a predetermined angle from a particle beam axis of travel of one embodiment of the present invention. Particle gun 202 may be configured to emit a particle beam along particle beam axis 510 toward first target layer 203. X-ray collimator 205 may be positioned such that a relative angle α exists between particle beam axis 510 and an X-ray axis 512 of X-rays that are transmitted through collimator 205, as illustrated in FIG. 5. In one embodiment of the present invention, angle α may be at least 50 degrees. Angle α may, for example, be between 50 degrees and 89 degrees, 65 degrees and 87 degrees, or 75 degrees and 85 degrees, inclusive, or any other integer or non-integer number of degrees within or between the enumerated ranges. In another embodiment, angle α may be between 67.5 degrees and 72.5 degrees, 72.5 degrees and 77.5 degrees, or 77.5 degrees and 82.5 degrees, inclusive. Particle beam axis 510 may, as illustrated in FIG. 5, be normal to faces of first target layer 203 but may also be at an angle, e.g., up to 30, 45, 60, or 80 degrees, from normal incidence.

X-rays may be emitted in a plurality of directions from second target layer 204. However, the positioning of X-ray collimator 205, e.g., within an otherwise attenuating housing structure, can limit X-rays emitted from source 501 to those emitted along axis 512 or within a solid angle around said axis. The size of said solid angle may be determined by the aperture size of collimator 205 and distance of collimator 205 from second target layer 204. In the embodiment of FIG. 5, X-ray collimator 205 may have an aperture with a diameter between 150 µm and 4 mm, inclusive, or any integer or non-integer number of micrometers or millimeters within the enumerated range. X-ray collimator may, for example, have an aperture with a diameter between 200 µm and 400 µm, 400 µm and 600 µm, or 600 µm and 800 µm, inclusive. Collimator 205 may be positioned within 1 cm, 2 mm, 1.5 mm, or 1 mm from second target layer 204. In another embodiment of the present invention, angle α, size of and distance to collimator 205, or other collimation aspects of the source can be tailored to control the amounts of fluorescence radiation and Bremsstrahlung radiation being transmitted through collimator 205, e.g., to increase the amount of fluorescence radiation relative to Bremsstrahlung radiation being transmitted.

Figure 6:
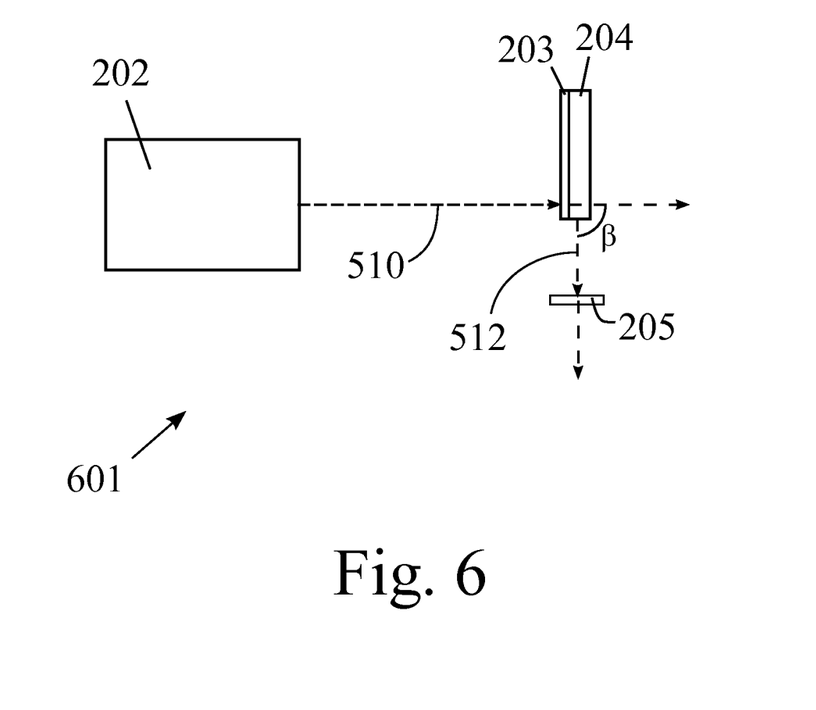
FIG. 6 is a diagram showing an X-ray source configuration having an X-ray collimator positioned at an approximately perpendicular angle to a charged particle beam axis of one embodiment of the present invention.

FIG. 6 is a diagram showing an X-ray source configuration having an X-ray collimator positioned at an approximately perpendicular angle to a particle beam axis of one embodiment of the present invention. In this embodiment particle gun 202 may be configured, e.g., positioned relative to first target layer 203, such that particle beam axis 510 intersects first target layer 203 within 400 µm of an edge of first target layer 203. Particle gun 202 may further be configured such that particle beam axis 510 intersects first target layer 203 within 300 µm, 200 µm, or 100 µm of an edge of first target layer 203. As illustrated in FIG. 5, X-ray collimator 205 may be positioned such that an angle β between particle beam axis 510 and X-ray axis 512 of X-rays that will be transmitted out of X-ray source 601 through collimator 205 is approximately 90 degrees. Angle β may, for example, be between 80 degrees and 100 degrees, 85 degrees and 95 degrees, or 87.5 degrees and 92.5 degrees, inclusive, or any other integer or non-integer number of degrees within the enumerated ranges. Fluorescence radiation may be emitted from an outer edge or surface of second target layer 204 in this embodiment.

Figure 7:
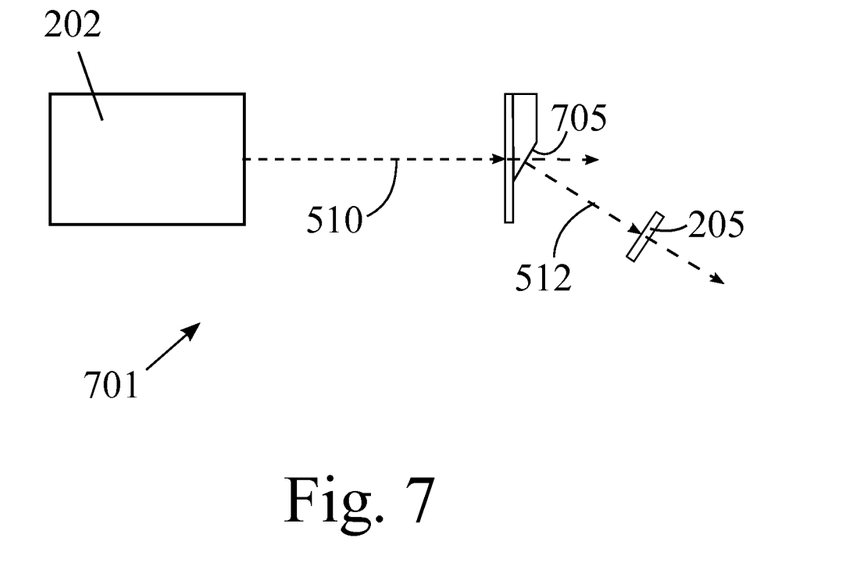
FIG. 7 is a diagram showing a multilayer X-ray target wherein the second target layer comprises a region of decreasing thickness of one embodiment of the present invention.

FIG. 7 is a diagram showing a multilayer X-ray target wherein the second target layer comprises a region of decreasing thickness of one embodiment of the present invention. In this embodiment second target layer 204 may be configured to have an angled face 705, e.g., a decreasing thickness toward one edge of the layer. An acute angle between the face of first target layer 203 in contact with second layer 204 and angled face 705 of second target layer 204 may be any angle less than 90 degrees, including but not limited to between 45 degrees and 90 degrees, inclusive. In one embodiment, the acute angle between these two faces of second target layer 204 may be between 45 degrees and 75 degrees, inclusive, or any other integer or non-integer number of degrees within the enumerated range. Angled face 705 may be a planar surface, e.g., such that second target layer 204 has a region of linearly decreasing thickness, but alternatively may have any amount of convex or concave curvature.

Second target layer 204 in the embodiment of FIG. 7 may have a maximum thickness relatively greater than previously described embodiments, e.g., while tapering down to a minimum thickness just above 0 µm or any of the previously enumerated thicknesses for a second target layer. Second target layer 204 may, for example, comprise a layer of material having a maximum thickness up to 1 cm. In one embodiment, second target layer 204 may have a maximum thickness up to 5 mm, 4 mm, 3 mm, 2 mm, or 1 mm. In another embodiment, second target layer 205 may have a maximum thickness up to 900 µm, 750 µm, 500 µm, or 350 µm, inclusive, or any other thickness between or below the enumerated values.

In the embodiment of FIG. 7, particle gun 202 may be configured for particle beam axis 510 to intersect first target layer 203 adjacent to a region of decreasing thickness in second target layer 204. For example, angled face 705 may be located on particle beam axis 510. In another embodiment, X-ray collimator 205 can be configured to transmit X-ray emitted from angled face 705. For example, in one embodiment axis 512 of X-rays to be transmitted through X-ray collimator 205 may be approximately tangent to angled face 705, e.g., within 10 degrees of normal incidence with angled face 705. However, transmitted X-ray axis 205 may be at any other angle relative to angled face 705.

In the embodiment of FIG. 7 and similar embodiments, first target layer 203 may be circular, polygonal, square, ellipsoidal, rectangular, or any other shape. First target layer 203 may have a height, e.g., or diameter, between 1 mm and 15 mm, inclusive, excluding additional material that may be provided for bonding of housing structures or other elements of the source around edges of the target. The target may further have a height, e.g., or diameter, between 1.5 mm and 10 mm, 2 mm and 8 mm, 2.5 mm and 6 mm, or 3 mm and 5 mm, inclusive, or any other integer or non-integer number of millimeters within or between the enumerated ranges. Second target layer 204 may be semi-circular, polygonal, rectangular, semi-ellipsoidal, or any other shape. In one embodiment, second target layer 204 may have a height or diameter, e.g., in the vertical dimension of FIG. 7, between 20% and 80% of the height or diameter of first target layer 203. Second target layer 204 may further have a height between 25% and 75%, 30% and 70%, 35% and 65%, 40% and 60%, or 45% and 55% the height of first target layer 203, inclusive, or any other integer or non-integer percentage within the enumerated ranges.

Figure 8:
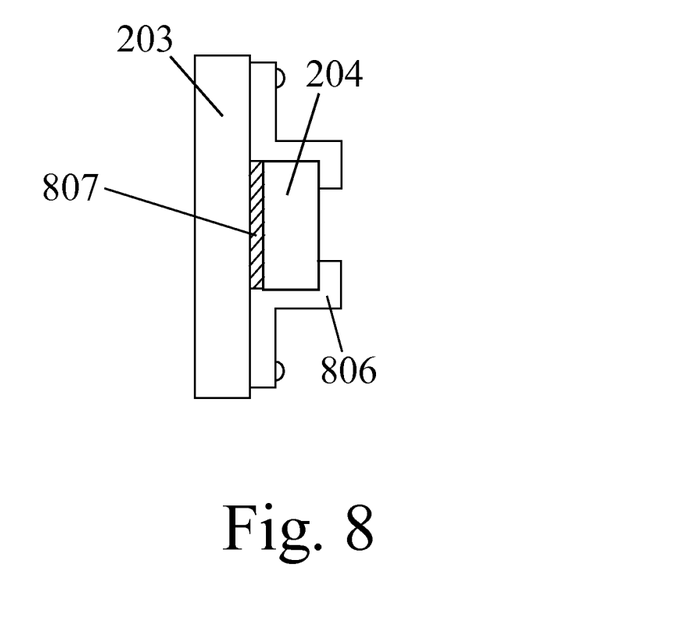
FIG. 8 is a diagram representing a multilayer X-ray target having a second layer positioned a predetermined distance from the first layer of one embodiment of the present invention.

FIG. 8 is a diagram representing a multilayer X-ray target having a second layer positioned a predetermined distance from the first layer of one embodiment of the present invention. In this embodiment, second target layer 204 may be a material configured for emission of X-ray fluorescence radiation, e.g., uranium, bismuth, or similar materials, and have any of the previously enumerated thicknesses for a second target layer. Similarly, first target layer 203 may be a material configured to emit Bremsstrahlung radiation, e.g., tungsten, molybdenum, or similar materials, and may have any of the previously enumerated thicknesses for a first target layer. Second target layer 204 may be positioned a predetermined distance from first target layer 203, e.g., by a mount structure 806 or similar structure. In one embodiment, the predetermined distance between first target layer 203 and second target layer 204 may be between 200 µm and 3 mm, inclusive. The distance between layers may, for example, be between 200 µm and 500 µm, 500 µm and 1 mm, 1 mm and 2 mm, or 2 mm and 3 mm, inclusive, or any other integer or non-integer number of micrometers or millimeters within or between the enumerated ranges. A gap left between first target layer 203 and second target layer 204 in these embodiments may be filled with an interface material 807, e.g., such as any of the thermally conductive or brazing materials that have been discussed.

Second target layer 204 may be matched in size, e.g., height or diameter, to first target layer 203, or may be relatively smaller as illustrated in FIG. 8. For example, second target layer 204 may have a height or diameter between 20% and 80% of the height or diameter of first target layer 203. In another embodiment, first target layer 203 may be within a vacuum chamber of the X-ray source, or form part of the containment of the vacuum chamber, while second target layer 204 can be outside of the vacuum. For example, in one embodiment first target layer 203 may be configured to hold vacuum within a vacuum chamber while mount structure 806 is attached to first target layer 203 and holds second target layer 204, e.g., outside of the vacuum chamber.

The embodiment of FIG. 8 may be particularly configured to remove or avoid thermal strain between first target layer 203 and second target layer 204, e.g., strain caused by a more rapid expansion of one layer than the other with temperature increases during X-ray generation. In embodiments of the present invention, first target layer 203 and second target layer 204 can have relatively matched or relatively different thermal coefficients of expansion.

In one embodiment of the present invention, a multilayer transmission target having a layer for X-ray fluorescence emission can be configured to implement an X-ray beam focal spot, e.g., spot on the layer from which fluorescence X-rays are emitted, less than or equal to 1 mm. Embodiments of the present invention may, for example, be configured for production of X-ray beam focal spots with diameters between 150 µm and 250 µm, 250 µm and 350 µm, 350 µm and 450 µm, 450 µm and 550 µm, 550 µm and 650 µm, 650 µm and 750 µm, 750 µm and 850 µm, or 850 µm and 950 µm, inclusive, or any other integer or non-integer number of micrometers within or between the enumerated ranges. Embodiments may alternatively be configured for production of beam focal spots with diameters up to 2 mm. Focal spot size may be related to the focusing of a particle beam onto the target, blurring of the beam occurring at interfaces of the target, and other aspects of beam physics. A multilayer target of an embodiment of the present invention may minimize blurring of the beam that can occur at interfaces, e.g., relative to reflection geometry sources of X-ray fluorescence. Focal spot size may affect the size of resulting X-ray beams.

In one embodiment of the present invention, an X-ray source having a multilayer target configured for X-ray fluorescence transmission can be utilized for X-ray fluorescence detection, e.g., identification of a predetermined material in a sample by exposure of the sample to X-ray photons sufficiently energetic to cause X-ray fluorescence in the predetermined material and subsequent detection of any resulting emission at the characteristic fluorescence energies of the predetermined material. A multilayer target in this embodiment may be configured to emit fluorescence X-rays having higher energies than at least a first inner shell binding energy or the K-edge of a material for detection. In one embodiment, the second target layer, e.g., the target layer configured to emit X-ray fluorescence in response to Bremsstrahlung emission from a first target layer, can comprise uranium. In another embodiment, the second target layer may comprise bismuth.

The size of the focal spot on the multilayer target may have any of the above enumerated diameters. In one embodiment, the focal spot can be sized to achieve, e.g., in possible conjunction with beam collimation, an X-ray beam diameter less than or equal to 400 µm at a distance of at least 2 cm from the X-ray window or collimator of the source. The focal spot may also be sized to achieve an X-ray beam diameter less than or equal to 350 µm, 300 µm, 250 µm, or 200 µm at this distance.

Figure 9:
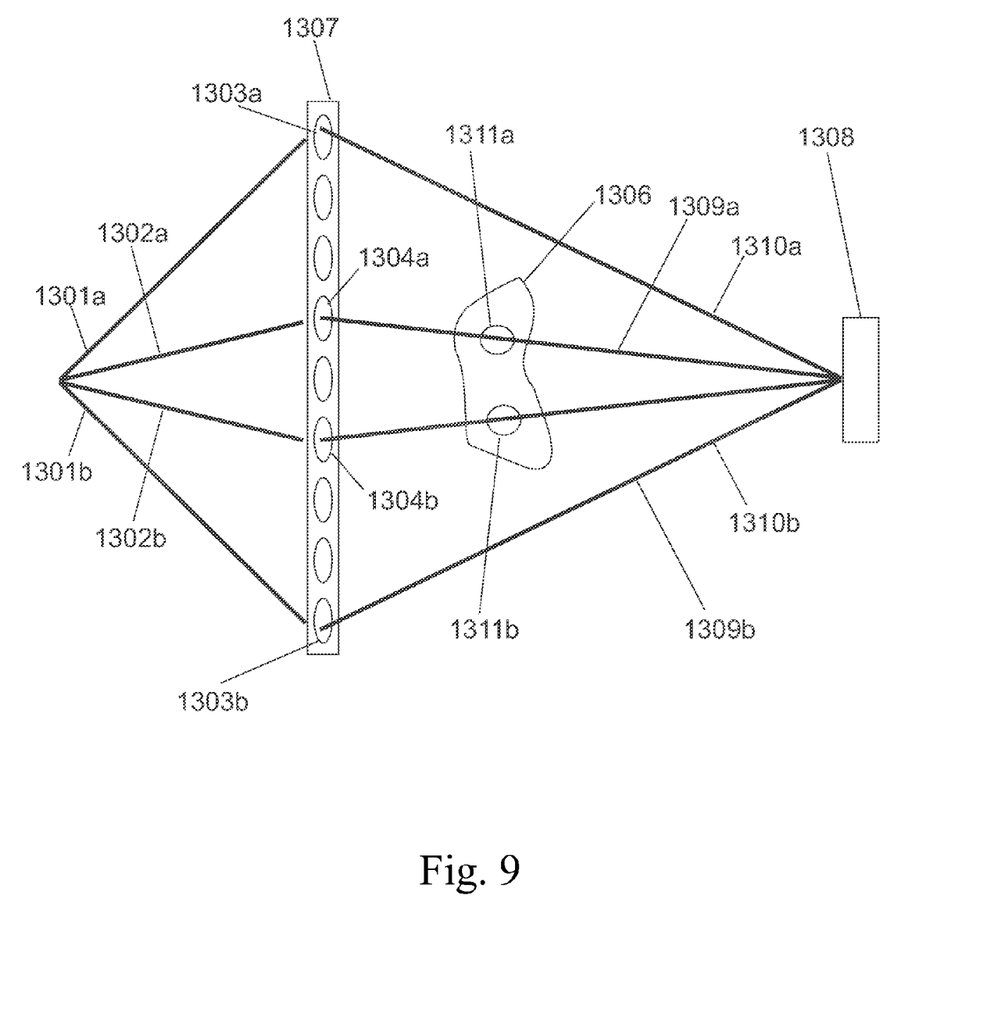
FIG. 9 is a diagram illustrating one embodiment of the present invention.

In another embodiment of the present invention, an X-ray source having a multilayer target configured for X-ray fluorescence transmission can be utilized for medical imaging, including but not limited to fluoroscopy, computed tomography, or similar X-ray imaging procedures. The X-ray source may have a single focal spot or be a scanning beam or multi-focal spot source. FIG. 9 is a diagram illustrating one embodiment of the present invention. In FIG. 9 electron beams 1301a and 1301b impinge on focal points 1304a and 1304b of target 1307. Here, for simplicity, only one row of focal spots is shown, whereas in another embodiment the target may be made of several rows of focal spots. When the electron beams 1302a and 1302b strike target 1307 at focal spots 1304a and 1304b, X-ray beams 1309a and 1309b are created and measured by detector(s) 1308.

In an embodiment of the present invention, detector 1308 is an energy resolving detector with two or more energy bins, such as 10 or less bins, 5 or less bins, or 2 bins, and the contrast-to-noise ratio can be optimized for a given contrast medium by weighting the number of detected X-rays in each bin by using the expression:

$$w(E) = \frac{1 - e^{-[\mu_c(E) - \mu_b(E)]d}}{1 + e^{-[\mu_c(E) - \mu_b(E)]d}}$$

as the weighting factor, wherein d is the thickness of the contrast medium, $\mu_c(E)$ is the energy dependent attenuation coefficient of the contrast medium, and $\mu_b(E)$ the attenuation coefficient of the background.

In another embodiment of the present invention, the exposure to X-rays of at least one person is optimized by modifying target 1307, and thereby modifying the shape of the X-ray energy spectrum, to best match the X-ray energy spectrum to one or more of: the needs of the procedure to be performed; the properties of the subject being imaged; the properties of the target organ to be imaged; and instrument that will be used during the procedure; or any contrast agents used during the procedure. The modification of target 1307 can involve the use of materials, wherein those materials are chosen from materials including but not limited to tungsten, copper, aluminum, beryllium, lead, rare earth elements including but not limited to gadolinium, and alloys or mixtures thereof.

It is an aspect of an embodiment of target 1307 that target 1307 comprises a tungsten layer in contact with the vacuum into which layer electron beam 1302 impinges and creates x-rays 1309, and wherein the x-ray spectrum is modified by one or more layers of an additional material or materials. The modified target 1307 can comprise a beryllium sheet onto which a film of tungsten is deposited, while beryllium is in contact with a thin layer of cooling water, which is followed by thin aluminum sheet, and wherein the procedure can utilize iodine as a contrast agent, and where the procedure can be a cardiac intervention. In an embodiment, there is at least one additional layer comprising at least one rare earth metal between the tungsten film and the beryllium sheet, where the at least one rare earth metal can comprise gadolinium.

Figure 10:
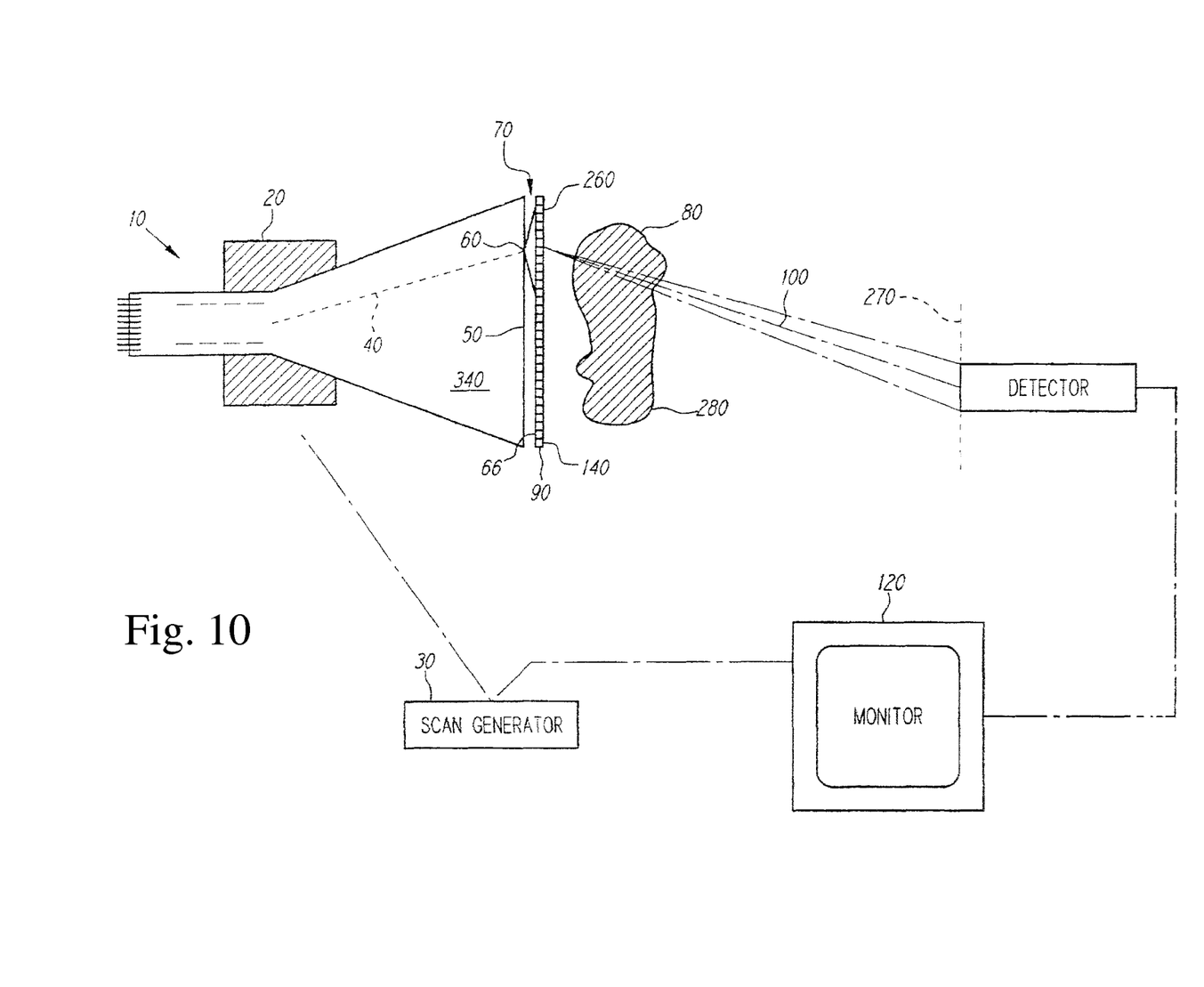
FIG. 10 is a diagram showing an exemplary scanning-beam X-ray imaging system of one embodiment of the present invention.

FIG. 10 is a diagram showing an exemplary scanning-beam X-ray imaging system of one embodiment of the present invention. X-ray source may, for example, be the X-ray source described more fully in U.S. Pat. Nos. 5,682,412 and 6,198,802, entitled "X-Ray Source" and "Scanning Beam X-ray Source and Assembly," respectively. X-ray source 10 can comprise deflection yoke 20 under the control of scan generator 30. Deflection yoke 20 can comprise one or more magnetic focus or deflection coils. The magnetic focus or deflection coils can be made with insulated electrical wire wound around a core. The core can be ferrite, steel, iron or other magnetic alloy. An electron beam 40 generated within X-ray source 10 can be scanned across target 50 within X-ray source 10 in a predetermined pattern. Target 50 can be a grounded anode target. The predetermined pattern can be a raster scan pattern, a serpentine, e.g., "S" shaped, pattern, a spiral pattern, a random pattern, a gaussian distribution pattern centered on a predetermined point of the target, or such other pattern as may be useful to the task at hand. However, aspects of the embodiment of FIG. 10 may also be implemented in stationary beam, e.g., single focal spot, X-ray source.

In one embodiment, a beam hardening filter can be brought into close proximity of the tungsten film in X-ray target 50 and the emitted K-line radiation can have a similar spatial extent as the primary radiation and can be useful for imaging. X-ray target 50 can also have an additional film with a rare earth that has K-lines particularly well suited for imaging. Specifically, the rare earth can provide large contrast in iodine, a contrast medium used in interventional cardiology. Various rare earths can be used, including but not limited to Er, Gd, Dy, or Sm, with different thicknesses, e.g., 10 μm to 150 μm, and X-ray tube potentials, e.g., 60 kVp to 90 kVp. In one embodiment, a 150 μm layer of erbium in X-ray target 50 at 80 kVp can result in a low dose. The dose can be 87% of that found with 1 mm iodine using 1 mm Copper beam hardening filter, 70 kVp X-ray tube potential and maximum electron beam current of 210 mA. A reduced Er layer thickness of 120 μm can also be used and Er can be used in X-ray target 50. For the beam hardening filter the dose can be 96% with 1 mm iodine using 1 mm Copper beam hardening filter, 70 kVp X-ray tube potential and maximum electron beam current of 210 mA and for the integrated case it can 89%. Thus, using Er in the target can save 7.5% of the dose compared to using it as a beam hardening filter.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. An X-ray source comprising:
   a particle gun configured to emit a beam of charged particles along a predetermined path;
   a first target layer of a first material positioned in said path, wherein said first material has an atomic number greater than 21;
   a second target layer of a second material positioned within 3 mm from said first target layer on opposite side of said first target layer than said path,
   wherein said second material has at least one characteristic X-ray fluorescence energy above 20 keV; and
   an X-ray collimator configured for selective transmission of X-rays emitted by said second target layer at a predetermined non-zero angle from an axis of travel of said beam.

2. The X-ray source of claim 1 wherein said second material is uranium.

3. The X-ray source of claim 1 wherein said predetermined non-zero angle is greater than 50 degrees.

4. The X-ray source of claim 1 wherein said predetermined non-zero angle is between 65 degrees and 87 degrees, inclusive.

5. The X-ray source of claim 1 wherein said first target layer and said second target layer are in contact with one another.

6. An X-ray source comprising:
   a particle gun configured to emit a beam of charged particles along a predetermined path;
   a first target layer of a first material positioned in said path, wherein said first material has an atomic number greater than 21;
   a second target layer of a second material positioned within 3 mm from said first target layer on opposite side of said first target layer than said path,
   wherein said second material has at least one characteristic X-ray fluorescence energy above 20 keV; and
   a layer of a thermally conductive material between said first target layer and said second target layer.

7. The X-ray source of claim 6 wherein said thermally conductive material is a cooling fluid.

8. The X-ray source of claim 6 wherein said characteristic X-ray fluorescence energy is above 80 keV.

9. An X-ray transmission target comprising:
- a first layer of a first material configured to receive a beam of charged particles on a first side and emit Bremsstrahlung radiation in response to said beam from a second side; and
- a second layer of a second material positioned within 3 mm of said second side configured to receive said Bremsstrahlung radiation on a first face and emit X-ray fluorescence radiation in response to said Bremsstrahlung radiation from a second face, wherein said second face is non-parallel to said first face.

10. The transmission target of claim 9 wherein said second material is uranium.

11. The transmission target of claim 9 wherein said second material is bismuth.

12. The transmission target of claim 9 wherein said first material is tungsten.

13. The transmission target of claim 9 wherein said first material is molybdenum.

14. The transmission target of claim 9 wherein thickness of said second layer is between 100 μm and 500 μm.

15. The transmission target of claim 9 wherein thickness of said first target layer is between 1 μm and 50 μm.

16. The transmission target of claim 9 wherein thickness of said first target layer is between 200 μm and 800 μm.

17. A method for generating an X-ray beam comprising:
- generating a beam of charged particles;
- accelerating said charged particles toward a first side of a first layer of a first material;
- emitting Bremsstrahlung radiation from a second side of said first layer;
- receiving said Bremsstrahlung radiation on a first face of a second layer of a second material, wherein said first face is located within 3 mm of said second side;
- emitting fluorescent X-rays from a second face of said second layer; and
- selectively transmitting said fluorescent X-rays emitted at angles greater than 50 degrees from an axis of travel of said beam of charged particles through an X-ray collimator.

* * * * *